(12) United States Patent
Frantz et al.

(10) Patent No.: US 7,194,296 B2
(45) Date of Patent: Mar. 20, 2007

(54) FLEXIBLE INSTRUMENT WITH OPTICAL SENSORS

(75) Inventors: Donald Dieter Frantz, Kitchener (CA); Paul David Clausen, Kitchener (CA); Terry Harold Fisher, Waterloo (CA); Stephen Eldon Leis, Waterloo (CA)

(73) Assignee: Northern Digital Inc., Waterloo (CA)

( * ) Notice: Subject to any disclaimer, the term of this patent is extended or adjusted under 35 U.S.C. 154(b) by 907 days.

(21) Appl. No.: 09/861,815

(22) Filed: May 21, 2001

(65) Prior Publication Data

US 2002/0052546 A1 May 2, 2002

Related U.S. Application Data

(63) Continuation of application No. 09/703,031, filed on Oct. 31, 2000, now abandoned.

(51) Int. Cl.
*A61B 19/00* (2006.01)

(52) U.S. Cl. .................. 600/424; 600/117; 600/145; 324/207.13; 250/227.14; 356/614

(58) Field of Classification Search .............. 600/407, 600/424, 117, 145; 362/554, 556; 324/244.1, 324/207.11, 207.13; 128/899; 901/47; 250/227.14–227.19; 356/32, 35.5, 614; 385/13
See application file for complete search history.

(56) References Cited

U.S. PATENT DOCUMENTS

| | | | | |
|---|---|---|---|---|
| 5,248,128 A * | 9/1993 | Warren et al. ........... 254/134.4 |
| 5,253,647 A * | 10/1993 | Takahashi et al. .......... 600/424 |
| 5,445,151 A * | 8/1995 | Darrow et al. .............. 600/419 |
| 5,447,156 A * | 9/1995 | Dumoulin et al. .......... 600/419 |
| 5,482,029 A * | 1/1996 | Sekiguchi et al. .......... 600/109 |
| 5,622,170 A * | 4/1997 | Schulz ....................... 600/424 |
| 5,695,501 A * | 12/1997 | Carol et al. ................. 606/130 |
| 5,715,822 A * | 2/1998 | Watkins et al. ............. 600/422 |
| 5,738,096 A * | 4/1998 | Ben-Haim .................. 600/407 |
| 5,828,770 A * | 10/1998 | Leis et al. ................... 382/103 |
| 5,831,260 A | 11/1998 | Hansen |
| 5,840,024 A | 11/1998 | Taniguchi et al. |
| 5,923,417 A * | 7/1999 | Leis ........................ 356/141.1 |
| 5,957,933 A * | 9/1999 | Yanof et al. ................ 606/130 |
| 6,073,043 A * | 6/2000 | Schneider ................... 600/424 |
| 6,127,672 A | 10/2000 | Danisch |
| 6,272,371 B1 * | 8/2001 | Shlomo ...................... 600/424 |
| 6,288,785 B1 * | 9/2001 | Frantz et al. ................ 356/614 |
| 6,470,205 B2 * | 10/2002 | Bosselman et al. ......... 600/424 |
| 6,471,710 B1 * | 10/2002 | Bucholtz .................... 606/130 |
| 2002/0052546 A1 * | 5/2002 | Frantz et al. ............... 600/424 |

FOREIGN PATENT DOCUMENTS

| WO | WO 94/23647 | 10/1994 |
| WO | WO 00/39576 | 7/2000 |

\* cited by examiner

*Primary Examiner*—Ruth S. Smith
(74) *Attorney, Agent, or Firm*—Fish & Richardson P.C.

(57) ABSTRACT

A flexible instrument includes a flexible member having a proximal portion, an intermediate portion, and a distal portion. At least one optical sensor positioned proximate the proximal portion of the flexible member provides a proximal end position signal indicative of the position of the proximal portion of the flexible member. At least one flexible member sensor positioned proximate one of the other portions of the flexible member provides a second position signal indicative of the position of the other portion of the flexible member.

19 Claims, 3 Drawing Sheets

FLEXIBLE INSTRUMENT WITH OPTICAL SENSORS

This application is a continuation of U.S. Ser. No. 09/703,031, filed on Oct. 31, 2000 now abandoned.

TECHNICAL FIELD

This invention relates to three-dimensional (3D) spatial positioning systems.

BACKGROUND

As is known in the art, it is desirable in many applications to accurately determine the spatial position (and sometimes the angular orientation, as well) of the distal tip of a flexible instrument. For example, in brachytherapy, it is necessary to implant a number of precisely spaced radioactive seeds into cancerous tumors inside the human body with a high degree of accuracy so that the radiation can be concentrated on the diseased tissue with a minimum of damage to surrounding healthy tissue.

The use of implantation needles to insert radioactive seeds is well known in the art, but these methods require a high degree of rigidity in the implantation needle to deliver the seeds accurately, as the target locations are assumed to lie on the needle's longitudinal axis. Since these needles are also necessarily thin to minimize tissue damage when driven into the body, they often are insufficiently rigid and so require elaborate support mechanisms to guide their insertion and to keep them as straight as possible. Despite this effort, bending of the needle occurs as it travels through the tissue, thus introducing substantial positional errors.

These errors could be reduced considerably if the end (or distal) tip of the needle could be accurately measured relative to the target location, such that any bending in the needle could be monitored, and compensation applied.

Other applications of such an instrument include, for example, catheters, endoscopes, and bronchoscopes, which are sufficiently thin and flexible to navigate interior passages of the human body.

General purpose instruments have been developed that incorporated bend and twist sensors distributed along their length at known intervals. These bend and twist sensors allow the user to approximate the tip position of the device by monitoring the manner in which the device "bends" and "twists" as it is moved in 3D space. A sensor data processing system is coupled to these bend and twist sensors and receives the flexure signals from these sensors. The processing system monitors the bend and twist sensors disposed along the device and extrapolates the device and tip position. This type of a system is known as a path-dependent measuring system; i.e., a system that requires knowledge of the spacing between each pair of sensors and a signal from each sensor to perform an extrapolation to determine the device's orientation. Particularly important is that, for path-dependent systems such as this, the distal end tip position is determined successively from intermediate measurements along the length of the flexible structure, beginning at a known location, typically the proximal end.

Path-dependent measurements of the distal end tip of a long thin flexible structure suffer from the inherent limitations of the end tip measurement being dependent upon a long chain of extrapolations from preceding measurements along the path. Small amounts of error in each location and orientation along the path can rapidly accumulate, resulting in a large buildup of error by the time the end of the path is reached.

The distal end tip of a thin flexible structure can also be determined by affixing a path-independent sensor to the distal end, such as a magnetic sensor, whose position can be tracked by a magnetic system employing a magnetic field generator, or an optical marker, whose position can be tracked by an optical system employing a number of light sensors. Such path-independent measurement devices provide direct position measurements and so are free of the extrapolation error accumulation inherent in path-dependent measurements, but they are subject to other limitations. For example, an optical distal end marker could not be used where the distal end was outside of the optical sensors' line of sight, such as in a medical instrument designed for insertion inside a patient's body, while a magnetic sensor would be subject to errors from magnetic disturbances and would be typically limited to smaller operational volumes. Such path-independent measurement devices do not have the robustness inherent in path-dependent devices employing several sensors.

SUMMARY

According to an aspect of this invention, a flexible instrument includes a flexible member having an intermediate portion and a distal tip. At least one intermediate sensor disposed at a predetermined point along the intermediate portion of the member provides an intermediate path signal indicative of the path of the intermediate portion of the flexible member. At least one distal sensor positioned proximate the distal tip of the flexible member provides a distal tip position signal indicative of the position of the distal tip of the flexible member.

Embodiments of this aspect of the invention may include one or more of the following features. The flexible instrument is configured to sense a controlled magnetic field. The controlled magnetic field is a three-dimensional magnetic field generated using a plurality of controlled magnetic coils. The at least one distal sensor includes a magnetic tip sensor for sensing the controlled magnetic field. The magnetic tip sensor is an inductive coil that provides the distal tip position signal which is indicative of the three-dimensional positioning of the distal tip of the flexible instrument within the controlled magnetic field. The at least one intermediate sensor includes at least one magnetic intermediate sensor positioned along the length of the intermediate portion of the flexible instrument, where the one magnetic intermediate sensor senses the controlled magnetic field. The magnetic intermediate sensor is an inductive coil that provides the intermediate path signal which is indicative of the three-dimensional path of the intermediate portion of the flexible instrument within the controlled magnetic field.

Embodiments of this aspect of the invention may include one or more of the following features. The intermediate sensor includes at least one fiber-optic sensor positioned along the length of the intermediate portion of the flexible instrument, where the fiber-optic sensor provides the intermediate path signal which is indicative of the three-dimensional path of the intermediate portion of the flexible instrument.

The fiber-optic sensor includes an optical flex sensor or an optical twist sensor. The optical sensor includes at least one optical fiber loop sensor having a light attenuation characteristic, which varies in accordance with the path of the intermediate portion of the flexible instrument. The optical fiber loop sensor includes a light source for generating a light signal which is transmitted through an optical fiber loop to a light sensor, where the attenuation of the light signal through the optical fiber loop is indicative of at least a portion of the three-dimensional path of the intermediate portion of the flexible instrument. The flexible instrument further includes a processor responsive to the intermediate path signal and the distal tip position signal to provide an indication, in a common reference frame, of the position and angular orientation of the distal tip and the intermediate portion of the flexible instrument.

According to a further aspect of this invention, the flexible instrument described above further includes a processor responsive to the intermediate path signal and the distal tip position signal which provides an indication, in a common reference frame, of the position and angular orientation of the distal tip and the intermediate portion of the flexible instrument.

According to a further aspect of this invention, a flexible instrument system includes a flexible member having an intermediate portion and a distal tip. At least one intermediate sensor disposed at a predetermined point along the intermediate portion of the member, the intermediate sensor providing an intermediate path signal indicative of the path of the intermediate portion of the flexible member. A pair of elements, one of the pair of elements being an energy transmitter and the other being an energy sensor, where one of the pair of elements is positioned proximate the distal tip of the flexible member and the other the element is positioned remotely, where the combination of the pair of elements provides a distal tip position signal indicative of the position of the distal tip of the flexible member.

Embodiments of this aspect of the invention may include one or more of the following features. The energy transmitter generates a controlled magnetic field. The energy transmitter includes at least one magnetic coil. The energy sensor senses the controlled magnetic field. The energy sensor includes at least one inductive coil. The energy transmitter is located proximate the distal tip of the flexible member. The energy sensor is located proximate the distal tip of the flexible member. The flexible instrument system further includes a processor responsive to the intermediate path signal and the distal tip position signal to provide an indication, in a common reference frame, of the position and angular orientation of the distal tip and the intermediate portion of the flexible instrument.

According to a further aspect of this invention, a flexible instrument includes a flexible member having an intermediate portion and a distal tip. At least one pair of elements, one element of each pair of elements being an energy transmitter and the other element of each pair of elements being an energy sensor, where one element of each pair of elements is positioned proximate the intermediate portion of the flexible instrument and the other element of each pair of elements is positioned remotely, where the combination of the at least one pair of elements provides an intermediate path signal indicative of the path of the intermediate portion of the flexible member. A pair of elements, one of the pair of elements being an energy transmitter and the other being an energy sensor, where one of the pair of elements is positioned proximate the distal tip of the flexible member and the other element is positioned remotely, where the combination of the pair of elements provides a distal tip position signal indicative of the position of the distal tip of the flexible member.

Embodiments of this aspect of the invention may include one or more of the following features. The flexible instrument further includes a processor responsive to the intermediate path signal and the distal tip position signal to provide an indication, in a common reference frame, of the position and angular orientation of the distal tip and the intermediate portion of the flexible instrument.

According to a further aspect of this invention, a method for determining the three-dimensional position of a flexible instrument having an intermediate portion and a distal tip includes controlling a magnetic field proximate the flexible instrument. The method includes generating an intermediate path signal indicative of the path of the intermediate portion of the flexible instrument. The method includes generating a distal tip position signal indicative of the position of the distal tip of the flexible instrument.

Embodiments of this aspect of the invention may include one or more of the following features. The method further includes processing the intermediate path signal and the distal tip position signal to provide an indication, in a common reference frame, of the position and angular orientation of the distal tip and the intermediate portion of the flexible instrument. Generating a distal tip signal includes sensing the magnetic field with a magnetic tip sensor positioned proximate the distal tip of the flexible instrument. Generating an intermediate path signal includes sensing the magnetic field with at least one magnetic intermediate sensor positioned along the length of the intermediate portion of the flexible instrument. Generating an intermediate path signal includes sensing the path of the intermediate portion with at least one fiber-optic sensor positioned along the length of the intermediate portion of the flexible instrument.

One or more advantages can be provided from the above. As the three-dimensional position of the distal end of the flexible instrument is directly read, it is not subject to extrapolation errors. Accordingly, the propagation and extrapolation errors associated with calculating the three-dimensional position of the intermediate portion of the flexible instrument are minimized. By directly reading the three-dimensional position of the distal tip of the flexible instrument, the path of the intermediate portion of the flexible instrument can be more accurately plotted. Further, as the flexible instrument combines directly read and indirectly read position sensors, the three-dimensional position of the flexible instrument can be accurately plotted, even if the accuracy of one of the sensors is comprised. The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

For the scope of this invention, we assume a very general notion of flexibility that ranges from highly flexible to nearly rigid, so that, e.g., a long thin steel needle subject to bending as it is inserted into the body is, for the purposes of this application, considered flexible. We denote such objects as "quasi-rigid" to differentiate them from less constrained flexible objects, which we denote as "fully flexible." More specifically, this invention combines a variety of sensor methods with various structural properties inherent in the device (such as the locations of the contained sensors and the material properties of the device) to enhance end tip measurements in a more reliable and robust manner.

Figure 1:
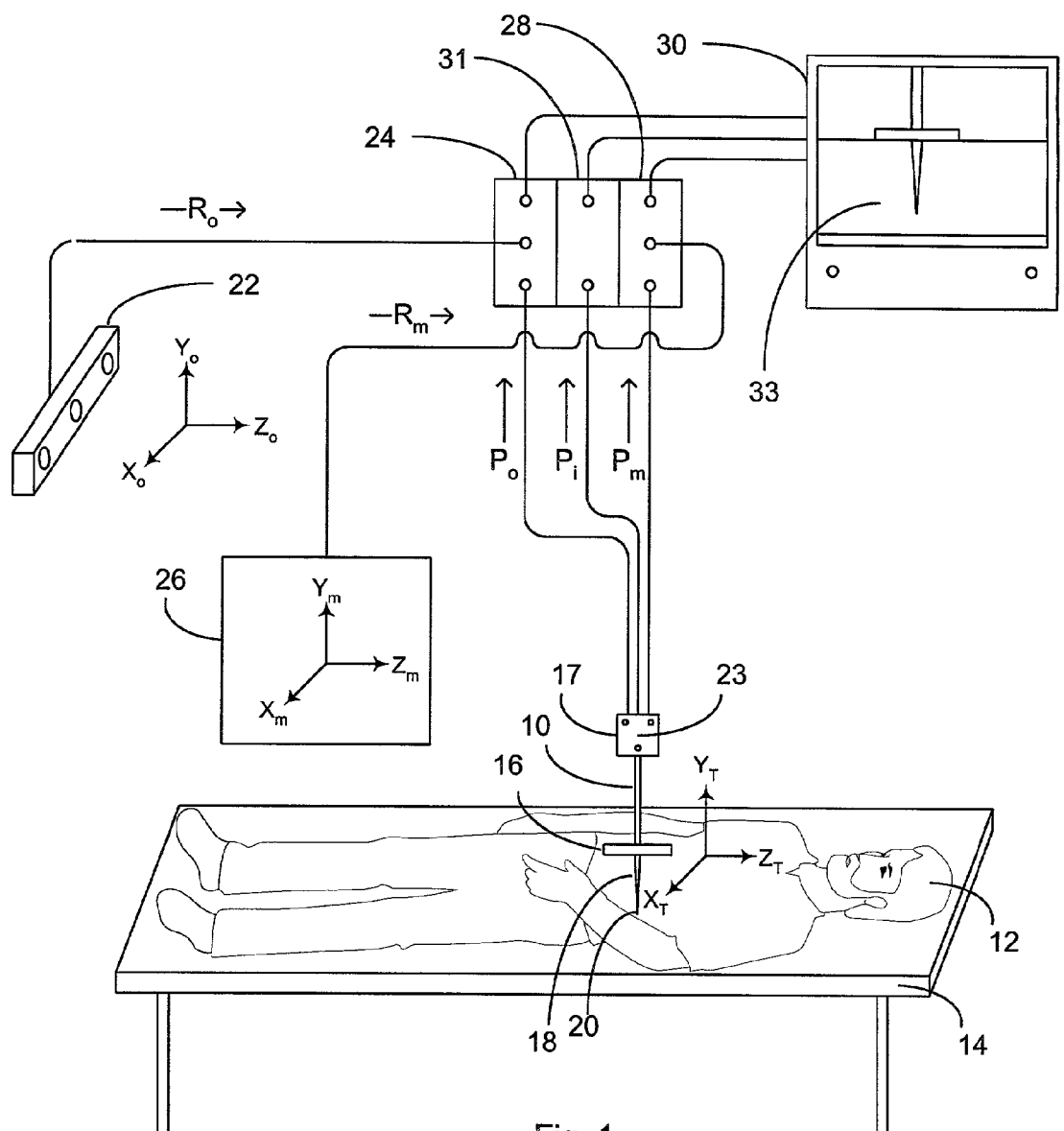
FIG. 1 is a diagrammatic view of the flexible instrument system.

Referring to FIG. 1, there is shown a flexible instrument 10 being utilized in a typical operating room setting in which a patient 12 is lying on an operating table 14. A rigid guide template 16 is used to assist in the insertion of flexible instrument 10 into patient 12. A common frame of reference ($X_t$, $Y_t$, $Z_t$) is provided with respect to rigid guide template 16. Flexible instrument 10 utilizes a combination of transmitting or sensing elements to monitor the position of proximal end 17, intermediate portion 18 and distal tip 20 of flexible instrument 10 with respect to patient 12. There are various different types of elements that can be used with flexible instrument 10, such as optical elements, fiber-optic elements, and magnetic elements.

In the event that the elements incorporated into flexible instrument 10 are optical sensors: a number of light emitting markers 23 affixed as a rigid body to proximal end 17 of flexible instrument 10; a camera 22 that is responsive to markers 23; and an optical system control unit 24, are utilized to determine the position of proximal end 17 of flexible instrument 10 within an optical frame of reference ($X_o$, $Y_o$, $Z_o$). An optical position signal $P_o$ is provided to optical system control unit 24 based on optical frame of reference ($X_o$, $Y_o$, $Z_o$).

If fiber-optic sensors are employed in flexible instrument 10, intermediate fiber-optic signal $P_I$ is provided to the fiber-optic system control unit 31 based on optical frame of reference ($X_o$, $Y_o$, $Z_o$) or a magnetic frame of reference ($X_m$, $Y_m$, $Z_m$; explained below in greater detail). Both the optical and fiber-optic subsystems 24 and 31 are connected to computer 30, where the external and internal signals $P_o$ and $P_I$ are superimposed onto a common frame of reference ($X_t$, $Y_t$, $Z_t$) by registration methods that are well known in the art.

Alternatively, in the event that the elements utilized in flexible instrument 10 are magnetic sensors or transmitters, a magnetic field generator 26 and a magnetic system control unit 28 are utilized to determine the position of flexible instrument 10 within a magnetic frame of reference ($X_m$, $Y_m$, $Z_m$). A magnetic position signal $P_m$ is provided to magnetic system control unit 28 based on magnetic frame of reference ($X_m$, $Y_m$, $Z_m$). Both optical subsystems 24 and 31 and magnetic subsystem 28 are connected to computer 30, where magnetic, fiber-optic, and optical position signals $P_o$, $P_I$, and $P_m$ are superimposed onto a common frame of reference ($X_t$, $Y_t$, $Z_t$). This, in turn, allows for easy viewing of the actual position of flexible instrument 10 within patient 12 on monitor 33 of computer 30. Please note that while optical system 24 utilizes optical frame of reference ($X_o$, $Y_o$, $Z_o$) and magnetic system 28 utilizes magnetic frame of reference ($X_m$, $Y_m$, $Z_m$), fiber-optic system 31 does not have its own frame of reference. Therefore, fiber-optic system 31 must be utilized in conjunction with another system (either optical or magnetic) so that fiber-optic system 31 can utilize that system's frame of reference for absolute positioning purposes.

It should be appreciated that while flexible instrument 10 is shown to be connected to both optical system control units 24 and 31 and a magnetic system control unit 28 (implying that the system is a hybrid optical/fiber-optic/magnetic system), this is for illustrative purposes only, as instrument 10 can utilize either pure optical components, pure fiber-optic components, pure magnetic components, any combination of two, or a combination of all three.

Figure 2:
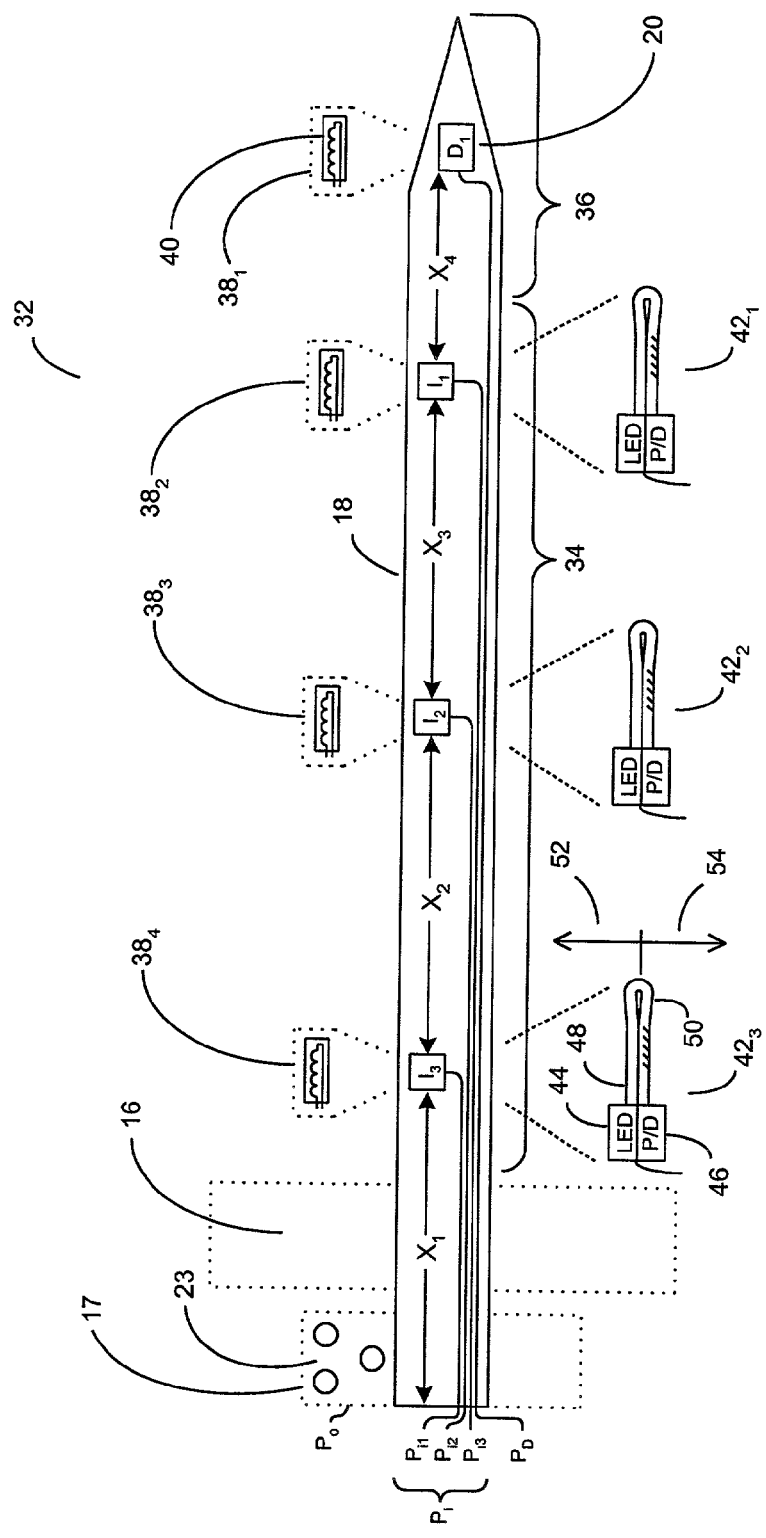
FIG. 2 is a detail view of the flexible instrument and its related sensors.
Figure 2:
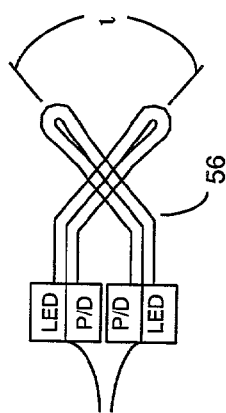

Referring to FIG. 2, there is shown a flexible instrument 10 having a flexible member 32 including proximal end 17 (with optical markers 23), intermediate portion 18, and distal tip 20. Flexible instrument 10 includes an intermediate sensor system 34 disposed at a predetermined point along intermediate portion 18 of flexible member 32. Intermediate sensor system 34 provides intermediate path signal $P_I$ (shown to be comprised of multiple discrete signals $P_{11}$, $P_{12}$, $P_{13}$) to the fiber-optic or magnetic control system (FIG. 1, items 31 and 28, respectively), where intermediate path signal $P_I$ is indicative of the path of intermediate portion 18 of flexible instrument 10.

Flexible instrument 10 includes a distal sensor 36 positioned proximate the distal tip 20 of flexible member 32. Distal sensor 36 provides distal tip position signal $P_D$ to the fiber-optic or magnetic control system (FIG. 1, items 31 and 28, respectively), where distal tip position signal $P_D$ is indicative of the position of distal tip 20 of flexible instrument 10.

While in this particular illustration, the intermediate sensor system 34 of flexible instrument 10 is shown to include three (3) discrete sensors $I_1$, $I_2$, and $I_3$, this is for illustrative purposes only. The actual number of intermediate sensors incorporated into flexible instrument 10 would be determined by the degree of resolution (and level of accuracy) required when displaying the path of intermediate portion 18 of flexible instrument 10. Specifically, as each sensor essentially provides a data sample along the path of intermediate portion 18 of flexible instrument 10, the higher the number of discrete sensors (and, therefore, samples), the greater the resolution and accuracy of the path displayed by the computer (FIG. 1, item 30). Similarly, while only one distal sensor $D_1$ is shown in this embodiment, other applications may require multiple distal sensors, such as a wide distal tip in which information concerning the exact tip placement is required or desired.

As stated above, the particular type of element (e.g. fiber-optic, magnetic, and so forth) that is utilized in flexible instrument 10 can be chosen in accordance with the user's preference or specific design criteria. In the event that flexible instrument 10 incorporates one or more magnetic sensors and transmitters, a magnetic field generator (FIG. 1, item 26) is utilized which generates a three-dimensional magnetic field and, therefore, a magnetic frame of reference ($X_m$, $Y_m$, $Z_m$). Typically, this magnetic field generator is a plurality of controlled magnetic coils arranged in a multi-dimensional format so that a multi-dimensional (or thee-dimensional) magnetic field is created about the patient.

In most applications, the distal sensor 36 positioned proximate distal tip 20 of flexible instrument 10 is a magnetic sensor $38_1$, where magnetic sensor $38_1$ typically incorporates an inductive coil 40. This is for illustrative purposes only, as any other appropriate functionally equivalent magnetic field sensor could be used, such as: a solid state magnetic field sensor; an iron core inductive coil, and so forth. As this inductive coil is moved through the magnetic field generated by the magnetic field generator, a current is induced in this coil which varies in proportion to the strength of the magnetic field sensed by the inductive coil. Therefore, as distal tip 20 is moved within the patient, the distal sensor 36 moves within the magnetic field. Accordingly, the strength of the current signal generated by inductive coil 40 within magnetic sensor $38_1$ will vary in accordance with its position within the magnetic field (and, therefore, the patient). This varying current signal generated by magnetic sensor $38_1$ within distal tip 20 is distal tip position signal $P_D$ which is provided to the appropriate control system for decoding. Accordingly, in this particular application, this distal tip position signal $P_D$ is provided to the magnetic control system (FIG. 1, item 28) so that the position of distal tip 20 can be determined in relation to the magnetic frame of reference $(X_m, Y_m, Z_m)$.

As stated above, flexible instrument 10 can use any combination of magnetic, fiber-optic, and/or optical sensors. Accordingly, intermediate sensor system 34, depending on the design criteria, may include magnetic sensors $38_2$, $38_3$, and $38_4$, which function in the same fashion a distal magnetic sensor $38_1$. As these particular sensors ($38_2$, $38_3$, and $38_4$) move through the magnetic field generated by the magnetic field generator (FIG. 1, item 26), a current is induced in each inductive coil embedded within each magnetic sensor. In this particular example, this results in the generation of three signals ($P_{11}$, $P_{12}$, and $P_{13}$) which are the current signals generated by the inductive coils of intermediate sensors $I_1$, $I_2$, and $I_3$ respectively. As these are magnetically-induced signals, signals $P_{11}$, $P_{12}$, and $P_{13}$ are provided to magnetic control system (FIG. 1, item 28) so that the path of the intermediate portion 18 of flexible instrument 10 can be determined in relation to the magnetic frame of reference $(X_m, Y_m, Z_m)$. This is possible since magnetic control system (FIG. 1, item 28) is receiving four (4) signals ($P_{11}$, $P_{12}$, $P_{13}$, and $P_D$), where the spacing of the sensors ($X_1$, $X_2$, $X_3$, and X known. In this particular example, where the distal tip sensor 36 and the intermediate sensors 34 are all magnetic sensors, this is a purely magnetic system and, therefore, a camera (FIG. 1, item 22) and an optical system control unit (FIG. 1, item 24) are not needed.

While thus far, we have been discussing the magnetic sensors as being passive inductive coils (or other functionally equivalent magnetic sensors), where a generated magnetic field induces a current in the individual magnetic sensors, this is purely a design choice. Alternatively, a small controlled current can be passed through each inductive element, where each element would generate its own magnetic field. These discrete magnetic fields could then be monitored by a three-dimensional magnetic field sensor (not shown) which could plot the three-dimensional position of each inductive element.

As stated above, the sensors utilized in flexible instrument 10 can be magnetic, optical, or fiber-optic. If fiber-optic intermediate sensors are employed, a fiber-optic system control unit (FIG. 1, item 31) is required. Optical intermediate sensors $42_1$, $42_2$, and $42_3$, would replace magnetic intermediate sensors $38_2$, $38_3$, and $38_4$ and provide the discrete component ($P_{11}$, $P_{12}$, and $P_{13}$) of intermediate path signal $P_I$. These signals are provided to fiber-optic system control unit (FIG. 1, item 31) and superimposed onto either the optical frame of reference ($X_o$, $Y_o$, $Z_o$) or the magnetic frame of reference ($X_m$, $Y_m$, $Z_m$) so that the path of intermediate portion 18 of flexible instrument 10 can be determined in relation to a common frame of reference ($X_t$, $Y_t$, $Z_t$).

Typically, optical intermediate sensors $42_1$, $42_2$, and $42_3$ are optical fiber loop sensors, which each incorporate a light source (typically a light emitting diode) 44, a light detector (e.g. a photosensor) 46, and a loop of fiber optic material 48. In these particular sensors, a portion of the covering of fiber optic loop 48 is modified (typically abraded) to create a lossy (or attenuating) light conductor, where the percentage of attenuation varies in relation to the curvature of the loop itself. Specifically, in this particular example, modified area 50 of fiber optic loop 48 is shown at the bottom of loop 48. In the event that fiber optic loop 48 is curved upward (in the direction of arrow 52), loop 50 will attenuate more light and, therefore, the light level sensed by light detector 46 will be reduced. Alternatively, when fiber optic loop 48 is curved downward (in the direction of arrow 54), the level of light attenuation will be decreased and, therefore, the light sensed by light detector 46 will be increased. Accordingly, these light detectors 46 provide a signal which varies in accordance with the curvature (and therefore the path) of intermediate portion 18 of flexible instrument 10. As is well known in the art, the optical fiber need not be fashioned in a loop, but can instead use a reflective end to return the transmitted light to light detector 46.

While the use of discrete magnetic sensors and optical sensors creates a system in which the position of the individual sensors can be directly read and obtained, the use of fiber-optic sensors creates a system which only allows for indirect determination of the path of intermediate portion 18. Specifically, since each fiber-optic sensor provides information concerning the curvature (or radius) of a particular discrete segment of intermediate portion 18 and the spacing of the sensors ($X_1$, $X_2$, $X_3$, and $X_4$) is known, the position of each sensor can be mathematically calculated. While the exclusive use of fiber-optic sensors would result in a system which shares the shortcomings of the path-dependant systems described above (the propagation of errors through each stage of the intermediate portion), the use of magnetic distal sensor $38_1$ (to pinpoint the location of distal tip 20 within the magnetic frame of reference ($X_m, Y_m, Z_m$)) and/or optical markers 23 (to pinpoint the location of proximal end 17 within the optical frame of reference ($X_o$, $Y_o$, $Z_o$)) minimizes these shortcomings. Specifically, since the distal magnetic sensor is directly positioned within the three-dimensional magnetic field, the effect of any error propagation can be minimized since the actual location of distal tip 20 is known. For example, if the calculated tip position determined using signals from fiber-optic intermediate sensors $42_1$, $42_2$, and $42_3$ states that distal tip 20 is 1 centimeter above the actual distal tip position (as determined by magnetic distal tip sensor $38_1$), this one centimeter error can be equally distributed amongst all stages of intermediate portion 18 and the actual path of intermediate portion 18 can be determined.

While the fiber-optic sensors discussed thus far have been traditional optical flex sensors, optical twist sensors 56 can be utilized which employ multiple optical loop sensors positioned in a manner which places the loops at an angle (θ) to each other. By comparing and processing the signals generated by each light detector, the twist of the optical fiber (along its axis) can be determined.

Figure 3:
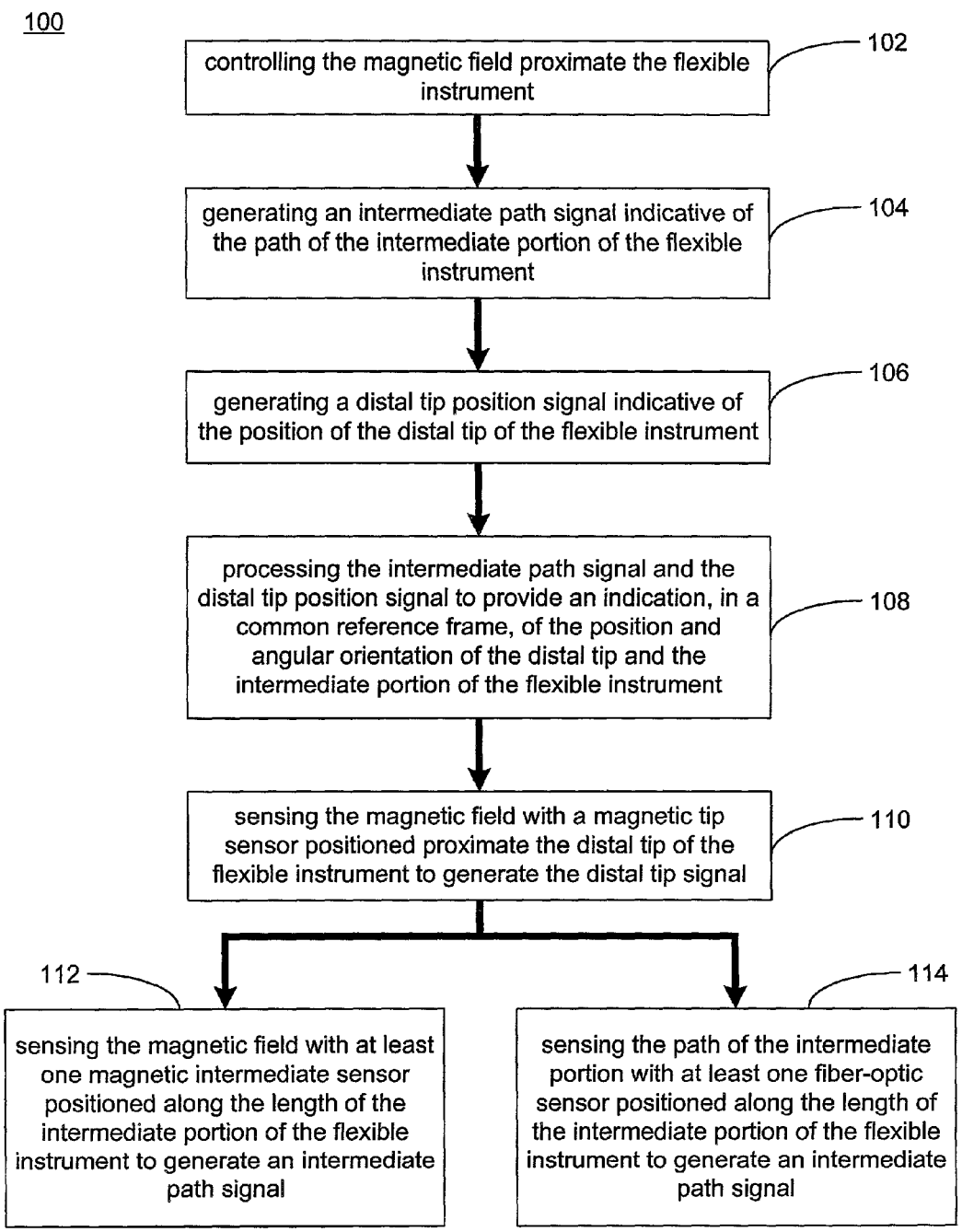
FIG. 3 is flow chart of the three-dimensional positioning method.

Now referring to FIG. 3, a method 100 for determining the three-dimensional position of a flexible instrument having an intermediate portion and a distal tip, includes controlling 102 a magnetic field proximate the flexible instrument. An intermediate path signal is generated 104 which is indicative of the path of the intermediate portion of the flexible instrument. A distal tip position signal is generated 106 which is indicative of the position of the distal tip of the flexible instrument. A remote computer system processes 108 the intermediate path signal and the distal tip position signal to provide an indication, in a common reference frame, of the position and angular orientation of the distal tip and the intermediate portion of the flexible instrument. If a magnetic distal tip sensor system, method 100 senses 110 the magnetic field with a magnetic tip sensor positioned proximate the distal tip of the flexible instrument to generate a distal tip signal. If a magnetic intermediate sensor system, method 100 senses 112 the magnetic field with at least one magnetic intermediate sensor positioned along the length of the intermediate portion of the flexible instrument, thus generating an intermediate path signal. If a fiber-optic intermediate sensor system, method 100 senses 114 the path of the intermediate portion with at least one fiber-optic sensor positioned along the length of the intermediate portion of the flexible instrument, thus generating an intermediate path signal. If the distal end position and orientation as measured and calculated by method 100 are in agreement to within the expected instrument tolerance, method 100 will report the position and use the position to refine all of the intermediate path sensor positions. Otherwise, method 100 will perform an error analysis to determine which subsystem is in error and report the more reliable position, or issue a warning if it cannot be determined which is reliable.

A number of embodiments of the invention have been described. Nevertheless, it will be understood that various modifications may be made without departing from the spirit and scope of the invention. For example, while flexible instrument 10 has been shown primarily used in a medical application, this is for illustrative purposes only. Flexible instrument 10 can be used in any application that requires the user to monitor the three-dimensional position of an object. For example, flexible instrument 10 can be incorporated into clothing so that the spatial orientation of the wearer's limbs can be monitored. This type of clothing material would be useful in virtual reality and special effects suits.

What is claimed is:

1. A flexible instrument, comprising:
   a flexible member having a proximal end and an intermediate portion;
   a plurality of optical sensors positioned at the proximal end of said flexible member for providing a proximal end position signal indicative of the position of the proximal end of said flexible member; and
   at least one fiber-optic sensor disposed at a predetermined point along the intermediate portion of said flexible member for providing an intermediate path signal which is independent of the proximal end position signal and indicative of the path of said intermediate portion of said flexible member.

2. The flexible instrument of claim 1 wherein said plurality of optical sensors include a plurality of light-emitting optical markers.

3. The flexible instrument of claim 1, further comprising at least one distal sensor positioned at a distal end of said flexible member for providing a distal tip position signal indicative of the position of said distal end of said flexible member.

4. The flexible instrument of claim 3 wherein said flexible instrument is configured to sense a controlled magnetic field.

5. The flexible instrument of claim 4 wherein said at least one distal sensor comprises a magnetic tip sensor for sensing said controlled magnetic field.

6. The flexible instrument of claim 5 wherein said magnetic tip sensor is an inductive coil that provides said distal tip position signal which is indicative of the three-dimensional positioning of said distal end of said flexible instrument within said controlled magnetic field.

7. The flexible instrument of claim 1, further comprising at least one magnetic sensor positioned along the length of said intermediate portion of said flexible instrument, where said at least one magnetic intermediate sensor senses a controlled magnetic field.

8. The flexible instrument of claim 7 wherein said at least one magnetic sensor is an inductive coil that provides an intermediate position signal which is independent of the proximal end position signal and indicative of the position of said intermediate portion of said flexible instrument within said controlled magnetic field.

9. The flexible instrument of claim 1 wherein said intermediate path signal is indicative of the three-dimensional path of said intermediate portion of said flexible instrument.

10. The flexible instrument of claim 1 wherein said at least one fiber-optic sensor includes a fiber-optic flex sensor.

11. The flexible instrument of claim 1 wherein said at least one fiber-optic sensor includes a fiber-optic twist sensor.

12. The flexible instrument of claim 1 wherein said at least one fiber-optic sensor includes at least one optical fiber loop sensor having a light attenuation characteristic which varies in accordance with the path of said intermediate portion of said flexible instrument.

13. The flexible instrument of claim 12 wherein said at least one optical fiber loop sensor includes a light source for generating a light signal which is transmitted through an optical fiber loop to a light sensor, where the attenuation of said light signal through said optical fiber loop is indicative of at least a portion of the three-dimensional path of said intermediate portion of said flexible instrument.

14. The flexible instrument of claim 1 further comprising a processor responsive to said proximal end position signal and said intermediate path signal for providing an indication, in a common reference frame, of the position and angular orientation of said proximal end and said intermediate portion of said flexible instrument.

15. A flexible instrument, comprising:
   a flexible member having a proximal end, an intermediate portion, and a distal end;
   a plurality of optical sensors positioned at said proximal end of said flexible member for providing a proximal end position signal indicative of the position of said proximal end of said flexible member;
   at least one fiber-optic sensor disposed at a predetermined point along the intermediate portion of said flexible member for providing an intermediate path signal which is independent of the proximal end position signal and indicative of the path of said intermediate portion of said flexible member; and
   a processor responsive to said proximal end position signal and said intermediate path signal for providing an indication, in a common reference frame, of the position and angular orientation of said proximal portion and said intermediate portion of said flexible instrument.

16. A method for determining the three-dimensional position of a flexible instrument having a proximal end and an intermediate portion, comprising:
   generating an intermediate path signal indicative of the path of the intermediate portion of the flexible member, wherein generating an intermediate path signal includes sensing the path of the intermediate portion with at least one fiber-optic sensor positioned along the length of the intermediate portion of the flexible instrument; and
   generating a proximal end position signal indicative of the position of the proximal end of the flexible member, wherein generating a proximal end position signal includes sensing the position of a plurality of light-emitting optical markers disposed at the proximal end of the flexible instrument within an optical frame of reference.

17. The method of claim 16 further comprising
   controlling a magnetic field proximate the flexible instrument; and
   generating a distal tip position signal indicative of the position of a distal end of the flexible member within the magnetic field.

18. The method of claim 17 wherein generating a distal tip position signal includes sensing the magnetic field with a magnetic tip sensor positioned at the distal end of the flexible instrument.

19. The method of claim 17 further comprising processing the intermediate path signal, the distal tip position signal, and the proximal end position signal to provide an indication, in a common reference frame, of the position and angular orientation of the distal end, the proximal end, and the intermediate portion of the flexible instrument.

* * * * *